United States Patent [19]

Cole et al.

[11] 4,382,895

[45] May 10, 1983

[54] PREPARATION OF ALKYL SULFONATES

[75] Inventors: Edward L. Cole, Fishkill; Robert M. Suggitt, Wappingers Falls, both of N.Y.

[73] Assignee: Texaco Inc., White Plains, N.Y.

[21] Appl. No.: 284,710

[22] Filed: Jul. 20, 1981

Related U.S. Application Data

[63] Continuation of Ser. No. 97,886, Nov. 27, 1979, abandoned.

[51] Int. Cl.$^3$ ............................................ C07C 143/24
[52] U.S. Cl. ............................ 260/505 P; 260/505 R; 260/505 S
[58] Field of Search ............. 260/505 R, 505 S, 505 P

[56] References Cited

U.S. PATENT DOCUMENTS 2,514,733  7/1950  Vold et al. ...................... 260/505 S

*Primary Examiner*—Alan Siegel
*Attorney, Agent, or Firm*—Carl G. Ries; Robert A. Kulason; George J. Darsa

[57] ABSTRACT

A process for the production of petroleum sulfonates from lubricating oil extract fractions wherein a primary extract-solvent mixture, preferably substantially free from water, is cooled to a temperature at least 25° C. below the extraction temperature to form two immiscible liquid phases comprising a secondary extract phase which is richer in aromatic hydrocarbons than the primary extract and a secondary raffinate phase which is poorer in aromatics than the primary extract. The secondary raffinate is sulfonated and the unsulfonated fraction returned to the separations process.

The process results in improved yields of petroleum sulfonates with lowered SO$_3$ consumption and less byproduct sludge than conventional processes in which the entire extract fraction is sulfonated.

5 Claims, 1 Drawing Figure

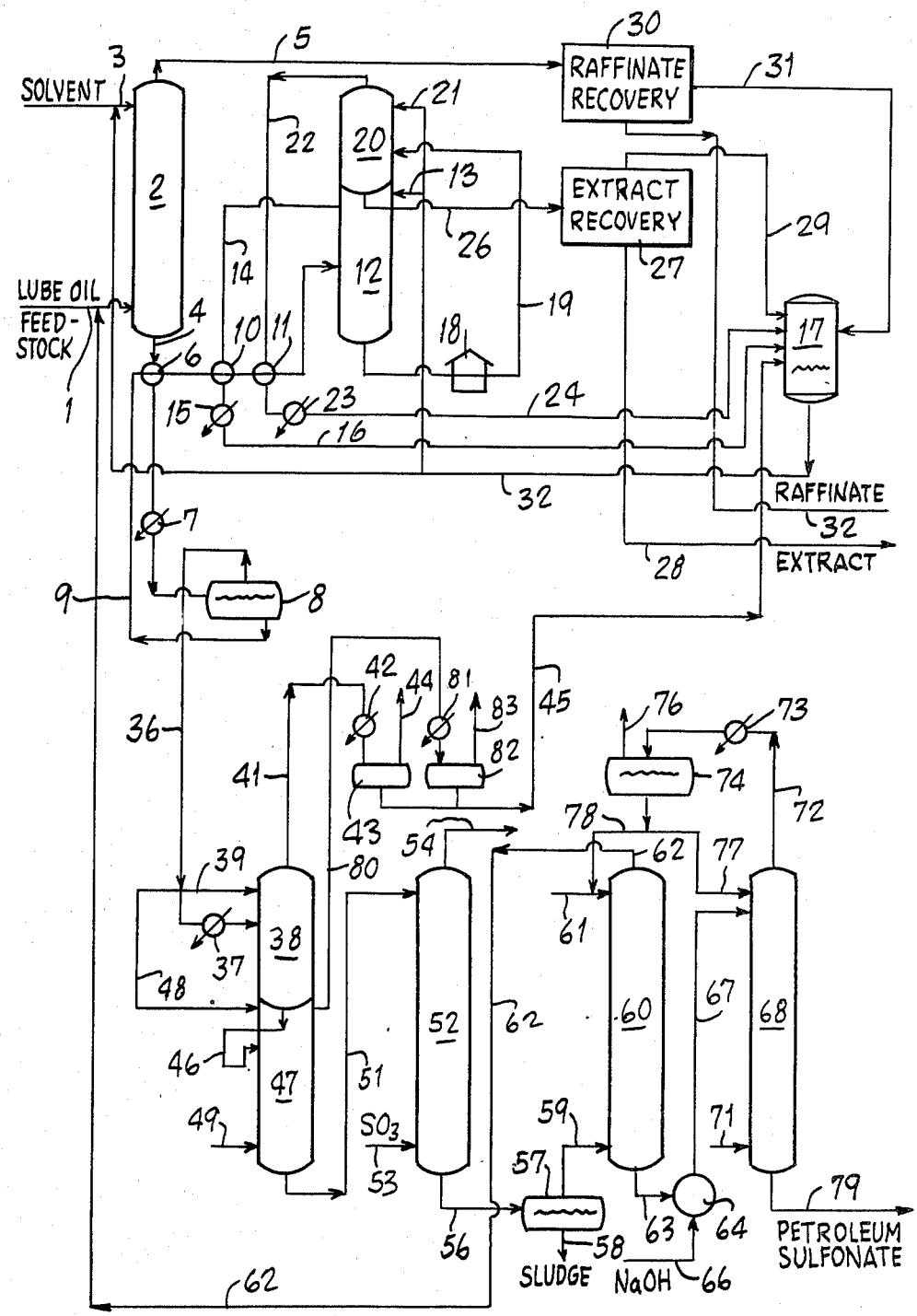

PREPARATION OF ALKYL SULFONATES

This application is a continuation, of application Ser. No. 97,886, filed Nov. 27, 1979, now abandoned.

The invention relates to an improved process for the preparation of alkyl sulfonates from petroleum oil feedstocks containing aromatic and non-aromatic constituents. In one of its more specific aspects, the invention relates to an improved method for the preparation of an improved sulfonation feedstock from the extract fraction obtained on solvent refining of a lubricating oil feedstock. A considerable savings in acid consumption is realized by the process of this invention as compared with conventional processes which produce petroleum sulfonates by sulfonation of extracts from lubricating oil solvent refining processes. In addition, the quantity of undesirable sludge, which presents a waste disposal problem, is substantially reduced.

It is well known that aromatic and unsaturated components of a lubricating oil basestock, such as those derived from crude petroleum by fractional distillation, may be separated from the more saturated hydrocarbon constituents of the mixture by various processes involving solvent extraction of the unsaturated and aromatic hydrocarbons. Foremost among the separations processes which have received commercial acceptance are extraction with furfural or N-methyl-2-pyrrolidone(NMP) as solvents.

The removal of aromatics and other undesirable constituents from lubricating oil base stocks improves the viscosity index, color, oxidative stability, thermal stability, and inhibition response of the base oils and of the ultimate lubricating oil products.

In the conventional solvent refining process, a hydrocarbon distillate, for example a lubricating oil feedstock, is contacted with a selective solvent for aromatic constituents of said feedstock, e.g., furfural or NMP, in an extraction zone whereby two phases are formed, a raffinate phase comprising a minor amount of solvent and an extract phase comprising a major amount of the solvent. The raffinate phase is separated from the extract phase and solvent is removed from each of said phases by fractional distillation processes, for example flash vaporization, distillation, rectification, stripping, or a combination of these operations.

It has been proposed heretofore to employ the extract phase, after separation from the raffinate phase and following the removal of solvent from the extract, as feedstock for the production of petroleum sulfonates by sulfonation with sulfur trioxide. In recent years, there has been an increased demand for low cost petroleum sulfonates for use in enhanced oil recovery operations. In such operations, the sulfonates are mixed with water and injected into partially depleted petroleum reservoirs to increase the recovery of crude oil therefrom. The extract fraction from lubricating oil refining processes has been utilized as one source of low cost feedstock for sulfonation to produce sulfonates useful in enhanced oil recovery operations. Ordinarily the preparation of the sulfonates from extracts from lubricating oil solvent refining operations is accompanied by high acid consumption and the formation of large quantities of undesirable sludges. The process of this invention provides a means for utilizing low cost extract from lubricating oil solvent refining operations as a source of raw material for the production of petroleum sulfonates with reduced acid consumption and reduced sludge formation.

The process of this invention involves the separation of an extract from conventional solvent refining processes into two fractions, one relatively richer in aromatic hydrocarbons than the conventional extract and the other relatively poorer in aromatic hydrocarbons than the conventional extract. It has been found that the ring sulfur compounds and multi-ring aromatic compounds are retained in the fraction relatively richer in aromatic compounds. These materials are undesirable as sulfonation feedstocks. The fraction relatively poorer in aromatic compounds contains a larger percentage of alkyl benzenes and indanes, which are more desirable feedstocks for sulfonation. The process of the invention, described in greater detail hereinafter, represents an improvement over those of the prior art.

In conventional lubricating oil refining processes, as applied to charge stocks from Mid-Continent or similar mixed base crude oils, the solvent extraction step is carried out under conditions effective to recover about 45 to 75 volume percent of the lubricating oil charge stock as raffinate, or refined oil, and to extract about 25 to 55 volume percent of the charge as an aromatic extract. In these processes, the lubricating oil stock is contacted with a solvent, for example furfural or N-methyl-2-pyrrolidone(NMP) at a temperature at least 25° C., preferably at least 50° C. below the temperature of complete miscibility of the lubricating oil charge stock in the solvent.

A number of solvents are known which have an affinity for at least one component of a mixed base lubricating oil charge stock and which are partially immiscible with the lubricating oil charge stock under conditions in the oil-solvent contacting zone. The two liquid phases which exist in the contacting zone generally consist essentially of an extract phase containing the major amount of the solvent together with dissolved aromatic components of the charge stock and a raffinate phase containing non-aromatic components of the charge stock together with a minor amount of solvent.

Solvents generally are employed at dosages of 100 to 600 volume percent basis the volume of the oil charge stock, and the solvent extraction is generally carried out at a temperature within the range of 50° to 120° C. (120° to 250° F.). Solvent dosages within the range of 100 to 300 volume percent and solvent extraction temperatures in the range of 50° to 85° C. (120° to 185° F.) are generally preferred.

Particularly preferred solvents are furfural and N-methyl-2-pyrrolidone, both of which are effective for the solvent extraction of aromatic components from lubricating oil charge stocks at relatively lower temperatures and lower solvent to oil dosages than most other known solvents. N-methyl-2-pyrrolidone is generally the most preferred solvent because of its chemical stability, low toxicity, and its ability to produce refined oils of improved quality. Some of the advantages which result from the use of N-methyl-2-pyrrolidone are detailed in U.S. Pat. No. 4,057,491.

In the extraction step, operating conditions are selected to produce a primary raffinate having a dewaxed viscosity index of about 85 to 100 and preferably about 90 to 96. When employing furfural as solvent, extraction temperatures within the range of 65° to 110° C. (150° to 230° F.), and preferably about 75° to 95° C. (165° to 205° F.), with solvent dosages within the range of about 150 to 600 percent are employed in order to provide the desired VI product. When N-methyl-2-pyrrolidone is employed as solvent, solvent extraction temperatures within the range of 60° to 100° C. (140° to 212° F.), preferably within the range of 65° to 95° C. (150° to 205° F.), with solvent dosages within the range of 100 to 500 percent, and preferably within the range of 150 to 400 percent, are suitable. The primary raffinate is separated from a primary extract in the extraction step and both are treated for the recovery of solvent for reuse in the process and for the recovery of a refined oil and an aromatic extract, both substantially free from solvent, as products. Various methods are employed for the separation and recovery of solvent from the extract and raffinate mixtures, the nature of the recovery system depending to some extent upon the particular solvent employed and whether or not the solvent also contains water as a moderator.

To produce a finished lubricating oil base stock, the primary raffinate is dewaxed to the desired pour point. If desired, the dewaxed oil may be subjected to a finishing treatment for color and stability improvement, for example mild hydrogenation.

The present invention provides a method of producing a third product from solvent extraction by the separation of the extract from the solvent extraction process into two separate fractions, one a secondary extract, which may be processed in the usual manner for the recovery of solvent and an extract product and the other, a secondary raffinate, which is processed for solvent recovery and the production of a sulfonate feedstock of improved quality. All other conditions remaining equal, the sulfonation of secondary raffinate in accordance with the present invention results in a petroleum sulfonate product of improved properties as compared with sulfonates produced by sulfonation of primary extract. At the same time, sulfuric acid consumption and sludge production are decreased. Details of the invention will be evident from the accompanying FIGURE and the following detailed description of a preferred embodiment of the present invention.

The FIGURE is a simplified schematic flow diagram illustrating the process of this invention as applied to a commercial solvent refining operation.

With reference to the FIGURE, lubricating oil feedstock is introduced through line 1 to an extraction tower 2 where it is intimately countercurrently contacted with solvent entering the upper portion of the extraction tower 2 through line 3. In the extraction tower 2, the lubricating oil feedstock is contacted with a selective solvent, e.g., furfural or N-methyl-2-pyrrolidone. The solvent extraction tower 2 typically is operated at a pressure in the range of 0 to 100 psig (1 to 8 bar) and preferably in the range of 20 to 50 psig (2.4 to 4.5 bar). The extract mixture, typically comprising about 85 percent solvent, is withdrawn from the bottom of extraction tower 2 through line 4. The raffinate mixture, typically comprising 85 percent hydrocarbon oil admixed with solvent, is discharged from the upper end of extraction tower 2 through line 5 and processed for the recovery of raffinate from the solvent as described hereinafter.

The major portion of the solvent appears in the extract mixture withdrawn from the bottom of extraction tower 2 through line 4.

The resulting primary extract is withdrawn from the bottom of extraction tower 2 through line 4 and passed through heat exchanger 6 which serves to cool the primary extract mixture and then to a cooler 7 wherein the primary extract mixture is further cooled to a temperature sufficiently lower than the temperature in extraction tower 2 to form two immiscible liquid phases. The cooled extract is introduced into decanter 8 wherein separation of the two phases occurs. Cooling of the primary extract from extraction tower 2 to a temperature approximately 25° C. (45° F.) or more below the temperature existing at the bottom of the extraction tower results in the formation of two liquid phases which are separated from one another by gravity in decanter 8. One of the liquid phases, a secondary extract, is relatively richer in aromatic hydrocarbons than the primary extract withdrawn from the extraction tower, and the other, a secondary raffinate, is relatively poorer in aromatic hydrocarbons than the primary extract.

The quantity of secondary raffinate produced depends upon a number of factors including the solvent-to-oil ratio in the extraction tower 2, the temperature at the outlet of the extraction tower, the character and composition of the solvent, the character and composition of the feedstock, and the temperature to which the primary extract is reduced prior to separation of secondary raffinate from a secondary extract. In general, under conventional solvent refining operations with feedstocks derived from Mid-Continent or similar mixed base crude oils, the secondary raffinate will contain some paraffinic hydrocarbons which may be returned to the process following the recovery of petroleum sulfonate therefrom.

A secondary extract phase is withdrawn from the lower part of decanter 8 and passed through line 9 to heat exchanger 6 in indirect heat exchange with the primary extract from extraction tower 2, thereby cooling the primary extract and heating the secondary extract. The secondary extract is then passed through heat exchangers 10 and 11 to low pressure fractionating column 12 for the recovery of solvent from the extract. Solvent is supplied to the upper part of fractionating column 12 through line 13 as reflux. Solvent separated from the secondary extract in low pressure fractionating column 12 is passed through line 14 to heat exchanger 10 wherein solvent vapors are cooled and condensed to preheat the feed stream to column 12 and then passed through cooler 15 and line 16 to solvent accumulator 17 for reuse in the process.

The unvaporized portion of the extract mixture withdrawn from the bottom of fractionation column 12 is passed through heater 18 and line 19 to a high pressure fractionating column 20. Solvent is supplied to the upper part of fractionating column 20 through line 21 as reflux.

The low pressure fractional distillation column 12 typically operates at a pressure in the range of 10 to 15 psig (1.7 to 2 bar) and the high pressure fractional distillation column 20 typically operates at a pressure in the range of 3.7 to 4.1 bar (40 to 45 psig).

A further amount of solvent is separated from the extract in fractionating column 20. The solvent vapors leaving the top of the fractionating column 20 through line 22 are passed through heat exchanger 11 in indirect heat exchange with the secondary extract mixture from the separator 8, condensing the solvent vapors and further preheating the secondary extract mixture prior to its introduction to low pressure fractionating column 12. The solvent is further cooled in cooler 23 and passed through line 24 to solvent accumulator 17 for reuse in the process.

The hydrocarbon oil extract withdrawn from the lower portion of fractionating column 20 through line 26 still contains some solvent, for example 5 to 15 volume percent solvent and 95 to 85 volume percent hydrocarbons. The extract withdrawn from the bottom of column 20 through line 26 is passed to an extract recovery system 27 wherein extract, usually containing less than 50 ppm solvent, is recovered as a product of the process. The extract recovery system may comprise a conventional combination of a flash tower and stripper, not illustrated in the drawing, or any other suitable extract recovery processing equipment. Product extract is discharged from the system through line 28 while recovered solvent is passed through line 29 to solvent accumulator 17 for reuse in the process.

Primary raffinate from the top of extraction tower 2 is passed through line 5 to a raffinate recovery system 30 wherein raffinate product is recovered from solvent in any suitable manner, for example by washing the raffinate with water or by a combination of flash vaporization and stripping, not illustrated in the drawing. Various methods are well known in the art.

Solvent separated from the primary raffinate in raffinate recovery system 30 is passed through line 31 to solvent accumulator 17 for reuse in the process. The recovered primary raffinate, containing less than about 50 ppm solvent, is discharged through line 32 as a solvent refined oil product of the process. Solvent from solvent accumulator 17 is recycled to the process via lines 32, 13, 21, and 3.

The secondary raffinate mixture from the upper part of decanter 8 is passed through line 36 to heater 37 wherein it is heated prior to introduction into flash tower 38 suitably maintained at subatmospheric pressure, such as commonly used for raffinate recovery in conventional commercial solvent refining operations, wherein solvent is separated from raffinate mixtures. A minor portion of the raffinate mixture from line 36 by-passes heater 37 and is introduced into the upper end of vacuum flash tower 38 through line 39 as reflux.

Solvent vapors separated from the secondary raffinate in flash tower 38 are withdrawn from the top of the tower and passed through line 41 to condenser 42 wherein the solvent vapors are condensed and the condensate collected in a condensate accumulator 43. Uncondensed gases are withdrawn through line 44, suitably to a vacuum system not illustrated in the drawing. Solvent recovered from the secondary raffinate is withdrawn from condensate accumulator 43 and passed through line 45 to solvent accumulator 17 for reuse in the process.

Secondary raffinate, still containing some solvent, is withdrawn from the lower part of vacuum flash tower 38 through line 46 into the upper end of a stripping column 47. A further portion of the secondary raffinate mixture from line 36 by-passes heater 37 and is introduced into the upper portion of stripper 47 through line 48 as reflux. In stripping column 47, residual solvent is removed from the secondary raffinate by stripping with a suitable stripping medium, for example steam or an inert gas, preferably an inert gas, entering the lower part of stripper 47 through line 49.

Raffinate, substantially free from solvent, is withdrawn from the lower part of stripper 47 and passed through line 51 to sulfonation tower 52 wherein the secondary raffinate at a temperature of about 60° C. to about 80° C. (about 140° F. to about 180° F.) is intimately contacted with a mixture of sulfur trioxide and an inert diluent gas, such as air, nitrogen, or sulfur dioxide, containing about 2.5 to 5 volume percent sulfur trioxide ($SO_3$) and supplied to the lower part of sulfonation tower 52 through line 53. The sulfonation reactor is of a known type, preferably of the type known in the art as a falling film reactor wherein sulfur trioxide and the secondary raffinate are brought into intimate contact with one another at a temperature in the range of about 75° C. to about 90° C. (about 165° F. to about 195° F.) preferably about 80° C. (about 180° F.) at a sulfur trioxide dosage of 7.5 to 9.5 weight percent, basis the weight of the raffinate charge to the reactor. Unreacted gases are discharged from the upper part of tower 52 through line 54.

The crude product from sulfonation tower 52 is passed through line 56 to a separator 57, suitably in the form of a gravity settler or decanter in which sludge formed during the sulfonation reaction is permitted to separate by gravity from the petroleum sulfonate and unreacted hydrocarbons. Separation of the sludge from the sulfonation reactor effluent preferably is carried out at a temperature in the range of 60° C. to 70° C. (about 140° F. to 160° F.). The sludge is withdrawn from the separator 57 through line 58 for disposal. Sludge-free sulfonated secondary raffinate is withdrawn from the upper part of decanter 57 through line 59 to extraction tower 60 wherein the petroleum sulfonate is separated from unreacted hydrocarbon oil.

Extraction tower 60 suitably comprises a countercurrent liquid-liquid contact column provided with suitable trays, packing material, or the like designed to provide intimate contact between liquid extract flowing downwardly through the tower and the crude sulfonated secondary raffinate flowing upwardly through the tower. An aqueous solution of isopropyl alcohol containing 50 weight percent isopropyl alcohol is introduced into the upper part of extraction tower 60 through line 61 as solvent for the petroleum sulfonate. The extraction is preferably carried out at a temperature in the range of 70° to 80° C. (about 160° F. to 180° F.) at a solvent dosage of about 16 weight percent basis the weight of the sulfonated secondary raffinate charged to the extraction zone. The mixture of isopropyl alcohol and water effects a substantially complete separation between the petroleum sulfonates and unreacted hydrocarbons. Unreacted hydrocarbons comprising essentially paraffinic constituents of the lubricating oil feedstock are discharged from the upper end of extraction tower 60 and passed through line 62 to line 5 into admixture with the fresh lubricating oil feedstock. The hydrocarbons recycled to line 5 through line 62 represent an increase in the yield of primary raffinate and hence the yield of solvent refined oil from the lubricating oil refining process.

The petroleum sulfonate extract is withdrawn from the lower part of extraction tower 60 through line 63 into a neutralizing tank 64 wherein it is intimately mixed with an aqueous solution of sodium hydroxide containing 12 to 50 weight percent sodium hydroxide introduced through line 66 in an amount sufficient to neutralize the sulfonic acid and form the sodium salt of the sulfonated oil. Sufficient caustic solution is employed to produce a pH in the range of 7 to 9.

The neutralized mixture of water, isopropyl alcohol and petroleum sulfonate is passed through line 67 to the upper part of stripper tower 68 for recovery of petroleum sulfonate product from water and isopropyl alcohol. Stripping steam is introduced into the lower part of column 68 through line 71. Stripper 68 is typically a countercurrent vapor-liquid contact column provided with bubble trays, cascade trays, or the like designed to provide intimate countercurrent contact between the liquid extract flowing downwardly through the tower and inert stripping gas or steam introduced into the lower portion of stripper 68 through line 71. A mixture of water and isopropyl alcohol vapors is taken overhead through line 72 to condenser 73 wherein it is cooled by an amount sufficient to condense the steam and alcohol vapors. The condensate is collected in a condensate accumulator 74 from which uncondensed vapors or gases are withdrawn through line 76. A part of the condensate from accumulator 74 is returned to stripping column 68 through line 77 as reflux. The major part of the condensate from accumulator 74 is passed through line 78 to the upper part of column 60 for reuse in the process. Petroleum sulfonate product is discharged from column 68 through line 79.

Vapors of the solvent stripped from the secondary raffinate in stripper 47, mixed with the gaseous stripping medium, are passed through line 80 to condenser 81 wherein the solvent vapors are condensed and the condensate solvent collected in a condensate accumulator 82. Uncondensed gases and vapors are discharged through line 83. Solvent recovered from the stripping medium in accumulator 82 is passed through line 45 to solvent accumulator 17 for reuse.

A preferred embodiment of the process of the invention and its advantages is illustrated in the following examples.

EXAMPLE 1

A wax distillate lubricating oil feedstock (WD-5) from a Mid-Continent crude oil was extracted with furfural as solvent at 82° C. with a solvent dosage of 165 volumes of furfural per 100 volumes of oil. The feedstock had the following physical characteristics:

| | |
|---|---|
| API Gravity | 30.2 |
| SUS VIS. at 100° F. (37.8° C.) | 1.9 |
| SUS VIS. at 210° F. (99° C.) | 39.3 |
| Carbon Residue, Percent | 0.10 |
| Pour Point, °F. | +80 |
| Pour Point, °C. | +26.7 |

The primary raffinate and primary extract mixtures resulting from the extraction with furfural under the specified conditions were separated from one another and the primary extract mixture separated into several portions. One portion of primary extract was stripped of solvent and analyzed with a High Mass Spectrometer for saturated and unsaturated hydrocarbons. A second portion of the primary extract was cooled to a temperature of 24° C. in accordance with the process of the subject invention forming two immiscible liquid phases. The two phases separated by gravity into an upper layer comprising a secondary raffinate mixture and a lower layer comprising a secondary extract mixture. The two layers were separated by decantation. The secondary raffinate mixture amounted to approximately 50 percent of the primary extract from the furfural extraction step. The secondary raffinate was washed with water to remove all of the furfural and analyzed with a High Mass Spectrometer for its aromatic and saturated hydrocarbon content. The results of the analysis of the aromatics portion of the primary extract and the secondary raffinate are shown in Table I below.

TABLE I

| | Percentages by Weight | |
|---|---|---|
| Hydrocarbon Types | Primary Extract | Secondary Raffinate I |
| Saturates | 18.9 | 31.2 |
| Aromatics | 81.1 | 68.8 |
| Benzenes | 10.3 | 12.1 |
| Indanes | 5.1 | 6.0 |
| Dinaphthenebenzenes | 6.2 | 7.2 |
| Naphthalenes | 1.8 | 1.7 |
| Acenaphthenes | 7.7 | 6.1 |
| Acenaphthylenes | 12.2 | 9.4 |
| Phenanthrenes | 9.6 | 5.2 |
| Pyrenes | 2.6 | 0.7 |
| Chrysenes | 2.8 | 2.5 |
| Benzothiophenes | 8.3 | 8.2 |
| Dibenzothiophenes | 13.8 | 9.1 |
| Naphthobenzothiophenes | 0.7 | 0.4 |

It will be observed that the reduction in aromatics was at the expense of ring sulfur compounds and multi-ring aromatic compounds with the enhancement of the more desirable alkylated benzenes and indanes. The separation of a secondary raffinate from the primary extract resulted in an increase of 17.5 percent in the benzenes and indanes, a reduction of 23.6 percent in the multi-ring aromatic compounds, and a reduction of 22.3 percent in the aromatic sulfur compounds.

The primary extract sample and the secondary raffinate sample were sulfonated at a temperature in the range of 80° to 90° C. in conventional laboratory apparatus using a stirred reactor. The crude sulfonated product was settled and an upper layer containing the sulfonated hydrocarbons decanted from a lower layer comprising sludge. The separated upper layer was then contacted with an aqueous solution of isopropyl alcohol (50 weight percent alcohol) to form two phases, an upper layer comprising unsulfonated hydrocarbons and a lower layer comprising sulfonated hydrocarbons. The two layers were separated by decantation and subsequently neutralized with sodium hydroxide solution converting the sulfonates to the sodium form. Water and alcohol were separated from the sodium sulfonate product. Results are shown in Table II.

TABLE II

| Sulfonation of Extract Fractions | | |
|---|---|---|
| Process Data | Primary Extract | Secondary Raffinate |
| SO$_3$ Dosage, Wt. % | 15.5 | 10.4 |
| Yield (kg/100 kg Organic Charge) | | |
| Sodium Sulfonate (100% Active) | 25.2 | 30.7 |
| Sodium Sulfonate (Total) | 44.7 | 51.0 |
| Recovered Oil | 28.0 | 39.2 |
| Sludge | 44.2 | 21.2 |

It will be noted that on the basis of 100 kg of primary extract, 44.2 kg of sludge were formed, whereas only 21.1 kg of sludge were formed on sulfonation of the secondary raffinate in accordance with the present process. The improved extract also gave a higher yield of active sodium sulfonate, i.e., 30.7 kg per 100 kg of charge stock were obtained with the secondary raffinate as compared with 25.2 kg obtained by sulfonation of the primary extract. Thus, by the conventional procedure 1.76 kg of sludge per kg of active sodium sulfonate are produced, whereas with the improved method of this invention 0.69 kg of sludge is produced per kg of active sodium sulfonate. Thus, not only is the efficiency of sulfonate production increased by the improved method of this invention, but also the efficiency of the utilization of SO₃ is improved. Sulfonation of the primary extract produced 1.6 kg of active sulfonate per kg of SO₃ consumed, whereas sulfonation of the secondary raffinate in accordance with this invention resulted in the production of 2.9 kg of active sulfonate per kg of SO₃ consumed.

EXAMPLE 1

Seven parts by volume of water were added to a portion of the primary extract mixture of Example 1. The water-furfural primary extract mixture was then cooled to 24° C. A secondary raffinate was obtained in an amount equivalent to 63 volume percent of the primary extract from the solvent extraction process. This secondary raffinate, after the separation of furfural and water therefrom, was analyzed by the High Mass Spectrometer with the results indicated in Table III.

TABLE III

| Hydrocarbon Types | Percentages by Weight Secondary Raffinate II |
|---|---|
| Saturates | 27.4 |
| Aromatics | 72.6 |
| Benzenes | 12.4 |
| Indanes | 6.2 |
| Dinaphthenebenzenes | 7.2 |
| Naphthalenes | 1.8 |
| Acenaphthenes | 6.5 |
| Phenanthrenes | 5.7 |
| Pyrenes | 0.9 |
| Chrysenes | 2.6 |
| Benzothiophenes | 8.6 |
| Dibenzothiophenes | 10.0 |
| Naphthobenzothiophenes | 0.5 |

When this secondary raffinate was sulfonated by the procedure outlined in Example 1, 1.55 kg of sludge were produced for each kg of active sodium sulfonate produced. The addition of water to the primary extract in this example to assist in the separation of a secondary raffinate resulted in a higher yield of secondary raffinate but one which was less desirable for the production of petroleum sulfonates than the secondary raffinate of Example 1 in which no water was added to the primary extract prior to cooling of the primary extract and separation of the secondary raffinate.

We claim:

1. In a method for the manufacture of water-soluble petroleum sulfonates by sulfonation of an extract fraction from solvent refining of a hydrocarbon lubricating oil feedstock wherein said lubricating oil feedstock is contacted with a selective solvent for aromatic constituents of said feedstock in an extraction zone thereby forming a raffinate phase comprising non-aromatic hydrocarbons and a primary extract phase comprising aromatic hydrocarbons, said raffinate phase is separated from said primary extract phase, and at least a portion of said primary extract phase is subjected to sulfonation to produce a petroleum sulfonate, the steps comprising:

(a) cooling said primary extract phase after separation from said raffinate phase to a temperature at least 28° C. below the temperature in said extraction zone thereby forming a secondary extract phase relatively richer in multi-ring and sulfur-containing aromatic hydrocarbons and a secondary raffinate phase relatively poorer in multi-ring and sulfur-containing aromatic hydrocarbons, (b) separating said secondary raffinate phase from said secondary extract phase, (c) separating secondary raffinate from said secondary raffinate phase, (d) subjecting said secondary raffinate to sulfonation by reaction with sulfur trioxide effecting conversion of a portion of said secondary raffinate to petroleum sulfonates with the concomitant formation of by-product sludge, (e) separating sludge from the reaction product of sulfur trioxide and said secondary raffinate, (f) contacting the resulting sludge-free reaction product with a selective solvent consisting of water and isopropyl alcohol in a second extraction zone forming a solvent-rich phase containing water-soluble petroleum sulfonates and an oil-rich phase comprising oil-soluble petroleum sulfonates and unreacted hydrocarbon constituents of said secondary raffinate, (g) separating said solvent-rich phase from said oil-rich phase, (h) contacting said solvent-rich phase with an aqueous alkaline sodium salt solution effecting conversion of said petroleum sulfonates to the sodium form, (i) recovering water soluble sodium petroleum sulfonates from said solvent-rich phase from step (h), and (j) introducing said oil-rich phase from step (f) comprising oil-soluble sulfonates and unreacted hydrocarbon constituents of said secondary raffinate into admixture with lubricating oil feedstock to said first extraction zone.

2. A process according to claim 1 wherein said secondary raffinate is reacted with sulfur trioxide at a temperature in the range of 75° to 90° C. and a sulfur trioxide dosage in the range of 7.5 to 9.5 weight percent of said secondary raffinate.

3. A process according to claim 1 wherein the temperature of said second extraction zone is within the range of 70° to 80° C.

4. A process according to claim 1 wherein said alkaline sodium salt is an aqueous solution of sodium hydroxide containing 12 to 50 weight percent sodium hydroxide supplied in an amount sufficient to produce a pH in the range of 7 to 9.

5. A process according to claim 3 wherein the solvent in said second extraction zone is an aqueous solution of isopropyl alcohol containing 50 weight percent isopropyl alcohol and the solvent dosage is about 16 weight percent basis the weight of the sludge-free sulfonation reaction product charged to the second extraction zone.

* * * * *